United States Patent [19]

Ullman

[11] Patent Number: 4,589,421
[45] Date of Patent: May 20, 1986

[54] SAMPLING DEVICE

[75] Inventor: Edwin F. Ullman, Atherton, Calif.

[73] Assignee: Syntex (U.S.A.) Inc., Palo Alto, Calif.

[21] Appl. No.: 589,430

[22] Filed: Mar. 14, 1984

[51] Int. Cl.⁴ .............................................. A61B 5/14
[52] U.S. Cl. .................................. 128/763; 128/766; 422/100
[58] Field of Search ......................... 128/760, 762–770; 73/864.01–864.03, 864.11–864.25; 422/100; 141/31

[56] References Cited

U.S. PATENT DOCUMENTS

| | | | |
|---|---|---|---|
| 3,108,591 | 10/1963 | Kolbas | 128/764 X |
| 3,848,581 | 11/1974 | Cinqualbre et al. | 128/762 |
| 4,003,262 | 1/1977 | Gerarde et al. | 128/763 X |
| 4,427,015 | 1/1984 | Redeaux, Jr. | 128/765 |

FOREIGN PATENT DOCUMENTS 1410990 5/1966 France .

Primary Examiner—Kyle L. Howell
Assistant Examiner—Francis J. Jaworski
Attorney, Agent, or Firm—Theodore J. Leitereg

[57] ABSTRACT

A sampling device is disclosed. The device comprises a capillary tube having a first orifice for collecting and dispensing a liquid at one end of the tube and a second orifice at the other end of the tube. A chamber encloses the second orifice. The device has a small opening to the outside atmosphere, other than the first orifice, communicating with the capillary tube. Also included is substantially non-compressible means movable with respect to said opening for concomitantly sealing said opening and forcing air from said chamber through said capillary tube.

21 Claims, 13 Drawing Figures

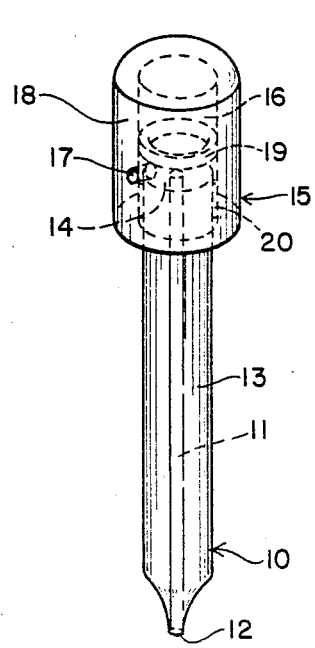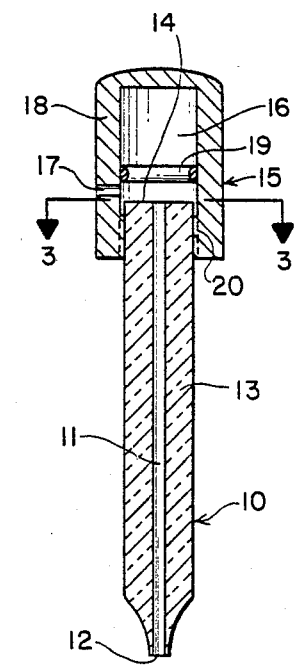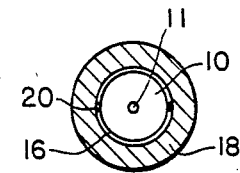
FIG. 1  FIG. 2  FIG. 3
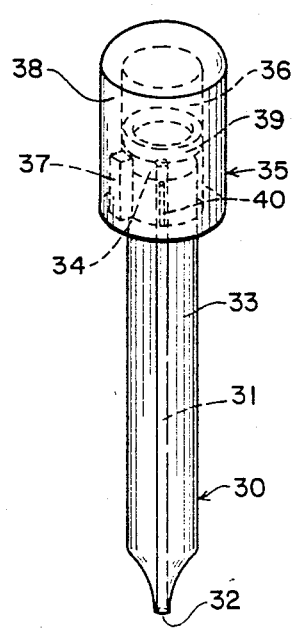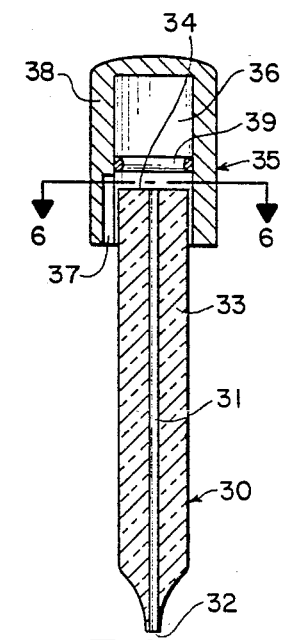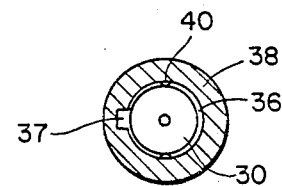
FIG. 4  FIG. 5  FIG. 6

FIG. 10
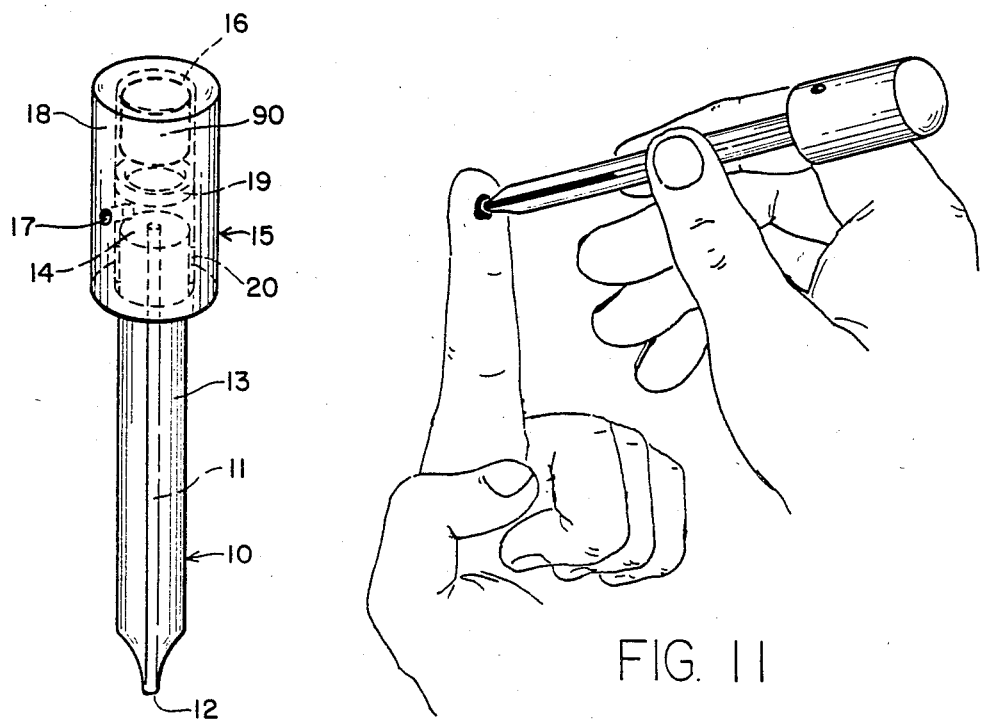
FIG. 11
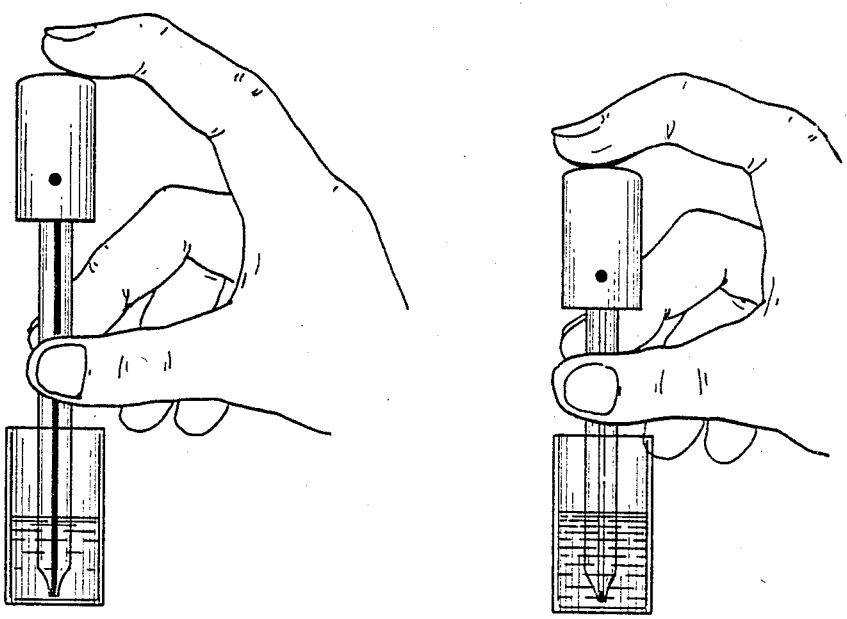
FIG. 12
FIG. 13

SAMPLING DEVICE

BACKGROUND OF THE INVENTION

1. Field of the Invention

This invention relates to devices for collecting and dispensing of liquids, particularly those liquids which are in a puddled form or in an open container. The device is particularly suited for the collection of blood from a blood drop.

Pipetting devices are known which employ capillary action to take a sample into the device. Such devices generally have a compressible (squeeze) bulb, usually with an opening in its wall. With the opening unobstructed, the sample fills a capillary tube. A finger is placed over the opening and the bulb is compressed to force the sample out of the tube. Manipulation of the squeeze bulb is, however, cumbersome. Such pipetting devices are not particularly useful in doctor's offices and diagnostic laboratories for taking small samples of, for example, blood from a puddle obtained by pricking a patient's finger.

Syringes for taking samples are also known. The syringe requires mechanical movements to fill the syringe with a sample and also to dispense the sample. Accurate sampling with a syringe usually requires a relatively expensive device. Ideally, the sampling portion of a sampling device should not be reusable. Consequently, the one-time use of a relatively expensive syringe is undesirable, but often unavoidable. In addition, the appearance of a syringe with a long needle often results in patient stress.

There is a need, therefore, for a sampling device which allows sampling without mechanical movement and dispensing of a precise amount of sample by means of mechanical movement.

2. Description of the Prior Art

A rinsing pipette is disclosed in U.S. Pat. No. 3,233,785. An apparatus for measuring precise microquantities of fluid samples is described in U.S. Pat. No. 4,003,262. A telescoping serum separator and dispenser is disclosed in U.S. Pat. No. 4,052,320. In U.S. Pat. No. 4,136,036 there is disclosed a collection and dispensing device for non-pressurized liquids. A device for the extraction of capillary blood is disclosed in U.S. Pat. No. 4,396,024.

SUMMARY OF THE INVENTION

The present invention is a sampling device for collecting and dispensing of liquids. The sampling device comprises a capillary tube which has a first orifice for collecting and dispensing a liquid at one of its ends and a second orifice at its other end. A chamber encloses the second orifice. The device has an opening to the outside atmosphere, other than the first orifice, communicating with the capillary tube. Also included is substantially non-compressible means movable with respect to the opening for concomitantly sealing the opening and forcing air from the chamber through the capillary tube.

The sampling device of the present invention thus has the advantage of allowing sampling of a liquid without mechanical movement such as that found in a syringe. Additionally, the present device has the advantage of having a simple action, similar to the action of a syringe, for dispensing a precise amount of sample. The use of cumbersome, and often inaccurate, squeeze bulbs is avoided. Also avoided is a syringe-like appearance.

BRIEF DESCRIPTION OF THE DRAWINGS

FIG. 1 is a broken side elevational view of a device in accordance with one embodiment of the present invention.

FIG. 2 is a cross-sectional view of the device of FIG. 1.

FIG. 3 is a cross-sectional view of the device of FIG. 2 along 3—3.

FIG. 4 is a broken side elevational view of another embodiment of a sampling device in accordance with the present invention.

FIG. 5 is a cross-sectional view of the sampling device of FIG. 3.

FIG. 6 is a cross-sectional view of the sampling device of FIG. 5 along 6—6.

FIG. 10 is a broken side elevational view of the device of FIG. 1 which further includes a capsule.

FIG. 11 is a side elevational view, partially broken, illustrating the use of the sampling device of FIG. 1 in the collection of blood from a blood drop.

FIG. 12 is a side elevational view, partially broken, illustrating the device of FIG. 1 in which the capillary passage is filled with blood which is about to be dispensed into a liquid.

FIG. 13 is a side elevational view, partially broken, of the device of FIG. 1 in which the contents of the capillary passage have been dispensed into a liquid.

DESCRIPTION OF THE SPECIFIC EMBODIMENTS

Figure 7:
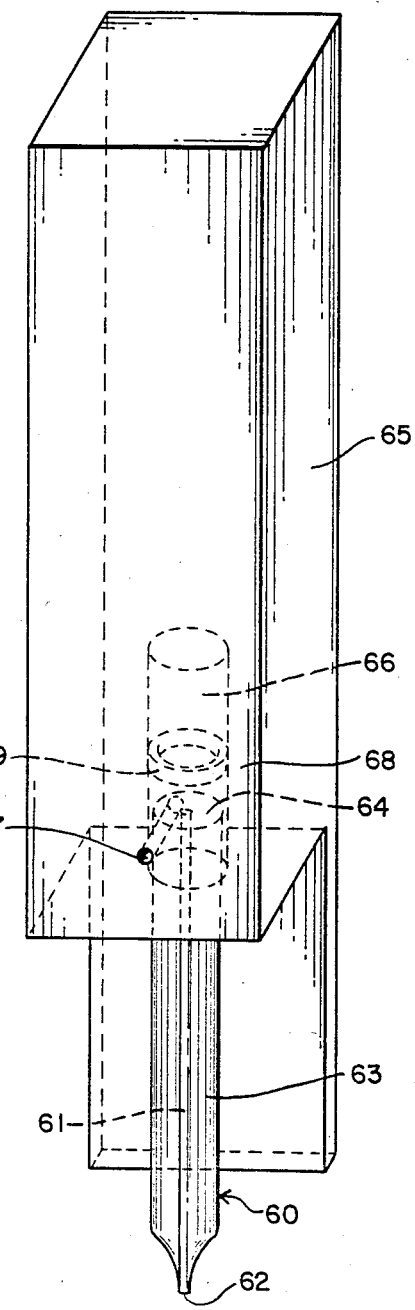
FIG. 7 is a broken side elevational view of another embodiment of a sampling device in accordance with the present invention where the device is in combination with an apparatus useful in a immunoassay.

The device of the present invention is useful for collecting and dispensing samples of liquid. In its broadest aspect the sampling device comprises a collection tube which has a capillary passage extending the entire length of the collection tube. The capillary passage has a collecting and dispensing orifice at one end of the tube and a second orifice at its other end. A chamber encloses the second orifice at the other end of the tube. The device has a small opening to the outside atmosphere other than that provided by the first orifice. The opening communicates with the capillary passage in the capillary tube and provides for pressure equalization between the interior and exterior of the chamber. Adjacent the chamber is substantially non-compressible, usually rigid, movable means. Generally, this means provides for concomitantly sealing the opening usually by moving at least one wall of the chamber relative to the opening. This movable means and the tube are in a first position which allows pressure equalization through the opening of the chamber and allows liquid to fill the capillary passage by means of capillary action. The movable means and the tube are manipulatable to a second position which prevents pressure equalization through the opening and defines a chamber volume which is greater than a predetermined volume of the capillary passage. Further movement of the means forces the defined volume of air from the chamber through the capillary passage and results in a dispensing of liquid in the capillary passage.

The sampling device of the present invention is particularly suited for collecting and dispensing serum and whole blood samples. However, any liquid which is capable of wetting the capillary surface so as to permit capillary migration in the capillary passage of the collection tube may be collected and dispensed using a sampling device in accordance with the present invention. Such other liquids include, but are not limited to, water, aqueous solutions, solvents such as alcohols, ethers, hydrocarbons, dimethylsulfoxide, formamides, esters, acids, amines, and the like.

In one aspect of the present invention, the sampling device comprises a housing having a chamber with a collection tube telescopically mounted therein. The collection tube has a capillary passage which extends from one end of the tube to the other. The capillary passage has a collecting and dispensing orifice at one end of the tube. The housing has a small opening extending to the outside atmosphere providing for pressure equalization which results from gas communication between the chamber and the extreme atmosphere. Sealing means are provided between the collection tube and the housing to prevent such pressure equilibration when the collection tube is moved past the opening. Liquid is drawn into the capillary by capillary action when the tube is in an extended position allowing such pressure equalization; liquid is ejected when the tube is moved into the chamber and pressure equalization is prevented, provided a chamber volume is defined which is greater than the volume of liquid to be ejected.

The term "capillary action" is used herein to refer to the force or phenomena obtained when the free surface of liquid being collected wets the confining walls of the capillary passage and the liquid surface, because of surface tension, moves along the confining walls of the capillary passage. More liquid is drawn into the capillary passage until a head of liquid is achieved in which gravity prevents further increase in liquid volume, until the source of liquid is removed, or until the entire capillary is filled.

The collection tube is telescopically mounted in the chamber in the housing in a first or extended position wherein pressure equalization with the atmosphere exists in the chamber as a result of the opening. The housing and the tube are movable to a second position wherein such pressure equalization is prevented by blocking of the opening and, if necessary, the use of sealing means between the tube and the housing. Simultaneously, a chamber volume is defined which is sufficient to permit the further movement of the tube to a retracted position and to provide a displacement of air sufficient to pressurize the chamber and forcibly eject the liquid from the capillary passage.

The sampling devices in accordance with the present invention can be further illustrated by reference to the attached drawings.

FIG. 1 is illustrative of one embodiment of a sampling device in accordance with the present invention. Collection tube 10 is provided with capillary passage 11, which has collecting and dispensing orifice 12 at one end of tube 10. Capillary passage 11 is formed by walls 13 of collection tube 10 and generally has a uniform cross-section. Collection tube 10 is preferably narrowed at the inlet orifice to provide for a more precise contact of orifice 12 with the liquid sample to be collected and to minimize wetting of the external surface of 10 and inaccuracy due to carryover. The other end (14) of the collection tube is mounted in a bore in housing 15 which forms chamber 16. The size of chamber 16 is designed to accommodate the end portion 14 of collection tube 10. Opening 17 extends from the exterior to the interior of housing 15, and has a diameter which will be sufficient to provide gas communication and pressure equalization between the exterior of 15 and chamber 16. Housing 15 with chamber 16 is formed by walls 18.

The inner dimensions of chamber 16 and the outer dimensions of collection tube 10, particularly above opening 17, will be such as to substantially limit the amount of gas which will escape around the tube. Thus, tube 10 must fit chamber 16 accordingly or sealing means 19 must be provided above 17 to prevent significant pressure loss when 10 is moved past opening 17 further into chamber 16. Exemplary of such sealing means are O-rings having suitable flexibility to allow collection tube 10 to be moved within chamber 16. Rubber O-rings may be used. However, other means for providing the gas tight seal between end 14 of collection tube 10 and chamber 16 above opening 17 will be suggested to those skilled in the art. For example, one may use a circumferential ridge on the inner wall of the chamber or one may use a suitable grease to achieve the sealing function.

Additionally, guide means 20 may be provided in chamber 16 below opening 17 in order to frictionally maintain tube 10 in chamber 16 in the event that a frictional fit is not realized without such guide means. The guide means may take the form of two or more longitudinal ribs in chamber 16 in a generally parallel relationship with the tube. The dimensions and composition of the sealing means will be such as to frictionally maintain tube 10 in chamber 16 and allow movement of tube 10 in chamber 16.

The inner dimensions of chamber 16 and the position of opening 17 therein, may be generally characterized according to the function which one desires to achieve in using the sampling device. When capillary passage 11 is filled with a liquid, it is desired to dispense such fluid through orifice 12. This may be achieved by manipulating the device generally by causing the housing to move in the direction of orifice 12, from the position shown in FIG. 1 to a position wherein pressure equalization is no longer achieved through opening 17 between the interior and exterior of housing 15. Thus, the inner dimensions of chamber 16 and the location of opening 17 should be such as to (a) allow accommodation of collection tube 10 and (b) permit collection tube 10 to be moved within housing 15 to a position which blocks fluid communication through opening 17 and (c) further permit the liquid in capillary passage 11 to be dispensed through orifice 12. Liquid is forced from capillary passage 11 when the collection tube passes opening 17 thus blocking pressure equalization. Air trapped in chamber 16 pushes the liquid in capillary passage 11 out of the collection tube through orifice 12. Thus, one characteristic of the sampling device of the present invention is that collecting and dispensing a liquid is achieved through the same orifice.

The sampling device of the present invention provides collecting and dispensing of precise predetermined amounts of a liquid. Collection of the liquid is obtained without precision pumping and positive displacement is provided to give a quantitative measure.

Capillary passage 11 will have dimensions which correspond exactly to the predetermined amount of liquid one desires to have dispensed. The particular volume of the capillary passage for any given device will depend upon the intended use of the device and the liquid to be sampled. The length of the passage should be less than the minimum height of the capillary action for the liquid to be sampled. Normally, a capacity of 0.1 to 100 microliters is considered to be a practical range. Often, the capacity of the passage will be less than 100 microliters, frequently less than 50 microliters, more usually less than 25 microliters. Volumes of liquids about 1.0 to 15.0 microliters can be conveniently measured.

The inner dimensions of chamber 16 and the placement of opening 17 within 16 will be such as to provide, after pressure equalibration is prevented through opening 17, a volume of air which is greater than the volume of liquid to be dispensed and thus is greater than the total volume of the capillary passage. Such a situation may be achieved, e.g., by sealing opening 17 at an early stage of movement of housing 15 in the direction of orifice 12. For the embodiment depicted in FIGS. 1 and 2, opening 17 may be close to the end of tube 10 enclosed by the chamber. Further movement of collection tube 10 toward orifice 12 allows one to dispense the entire precisely measured, predetermined amount of liquid from the capillary passage.

The walls of the capillary tube must have a thickness sufficient to achieve the forcing of the defined volume of air through the capillary passage and thus dispense the liquid contained therein. The capillary tube may be thin-walled with an outside diameter equal to about twice the inside diameter or it may be thick-walled with an outside diameter much greater than the inside diameter. The diameter of the capillary passage generally will be less than 2 mm, preferably less than 1 mm and normally greater than 0.1 mm.

For example, if one desires to obtain a sample of exactly 5 microliters of a liquid, the volume of capillary passage 11 will be exactly 5 microliters. The volume of inner chamber 16 located beyond opening 17 should have dimensions which define a volume in excess of 5 microliters so that air trapped in the chambers will be forced out through capillary passage 11. Any residual liquid that might otherwise remain on the walls of capillary passage 11 after dispensation is also ejected.

Sampling devices of the present invention can be manufactured from any suitable material. Illustrative of the considerations for the selection of a suitable material are (a) non-reactivity with and insolubility in the liquid sample to be collected, (b) sufficient rigidity to allow for the manipulation of the device in accordance with the invention, (c) wettability, (d) transparency, and (e) low temperature coefficient of expansion relative to the required accuracy of the device. Housing 14 and collection tube 10 may be made of the same material or they may be made of different material. The collection tube is preferably made of glass but may be made of any material that is substantially rigid or non-compressible, wettable, non-reactive, and insoluble with a low temperature coefficient of expansion. Preferably, the entire device will be made of transparent material to allow visual confirmation that the sample is fully drawn into and fully dispensed. The collection tube may be constructed of non-wettable material provided the capillary surface is coated with a wettable surfactant. The surfactant, of course, should not be reactive with the liquid being collected. The housing normally will not contact the liquid. The housing may be made of a substantially non-compressible material which allows a suitable interaction with the collection tube according to the function desired of the present device. The collection tube 10 should be movable within housing 15. Materials from which the sampling device of the present invention may be made include glass, synthetic rigid polymers or plastics, e.g., vinyl chloride-vinylidene chloride copolymer, polyesters, polystyrene, acrylics, and the like.

Another embodiment of the sampling device of the present invention is depicted in FIGS. 4–6. The numbering convention used in FIGS. 4–6 has been designed so that the second digit of the number is the same as the second digit of the number of the corresponding element found in the sampling device depicted in FIGS. 1–3. Capillary tube 30 with capillary passage 31 has orifice 32 at one end. The capillary passage is defined in tube 30 by wall 33. The other end (34) of capillary tube 30 is mounted in housing 35, which has chamber 36 defined by wall 39. Opening 37 in this particular embodiment is in the form of a longitudinal notch in wall 38 extending from the base of the wall to a point above top portion 34 of tube 32. Opening 37 provides pressure equalization between the exterior of the device and chamber 36. The device further includes sealing means 39. Capillary tube 30 is mounted in housing 35 in a first or extended position such that pressure equalization exists between the exterior of the device and the interior of chamber 36. In this way a liquid sample can be drawn into capillary passage 31 by the force of capillary action when the device is in a first, in this case, extended position. Collection tube 30 is movable within chamber 36 to a second position where pressure equalization is prevented through opening 37. Movement of collection tube 30 within chamber 36 beyond the second position and past sealing means 39 to a retracted position forces any liquid contained in capillary passage 31 out of the collection tube through inlet 32.

As mentioned earlier, the sampling device of the present invention is particularly suited for collecting puddled liquids such as blood from a blood drop produced by a pin prick. There are a number of situations in which collection of such sample is desirable. For example, in diagnostic methods collection of precise amounts of a sample of liquid may be required. The present device is particularly suited for use in conjunction with the collection of samples for performing an assay.

The sampling device of the present invention is suitable for use in conjunction with a diagnostic immunochemical test device. The present sampling device can be used separately from such test device to collect a sample. However, the present sampling device may also be an integral part of the test device.

An example of such a device is depicted in FIG. 7. The numbering convention used in FIG. 7 has been designed so that the second digit of the number is the same as the second digit of the number of the corresponding element found in the sampling device depicted in FIG. 1. Capillary tube 60 with capillary passage 61 has orifice 62 at one end. The capillary passage is defined in tube 60 by wall 63. The other end (64) of capillary tube 60 is mounted in housing 65, which housing serves a dual function. Housing 65 also accommodates a diagnostic test device such as an immunochemical strip which is found on the front of the test device and is not shown. Housing 65 has chamber 66 which is defined by wall 68 of housing 65. Small opening 67 provides pressure equalization between the exterior of the device and chamber 66. Capillary tube 60 is mounted in housing 65 in a first position such that pressure equalization exists between the exterior of the device and the interior of chamber 66. In this way a liquid sample, in this case a blood sample, is drawn into capillary passage 61 by the force of capillary action. Collection tube 60 is movable within chamber 66 to a second position where pressure equalization is prevented through opening 67. Movement of collection tube 60 within chamber 66 beyond the second position and through sealing means 69 forces any liquid contained in capillary passage 61 out of the collection tube through inlet 62.

The device depicted in FIG. 7 provides a number of advantages over a system where the sampling device and the test device are provided separately. The first advantage is that there is one less device to be dealt with in carrying out a diagnostic test. In addition, there would be a cost reduction in the manufacture of such a dual test device since one need not manufacture two separate devices, one for collecting and dispensing a sample and one for conducting the diagnostic test.

Figure 8:
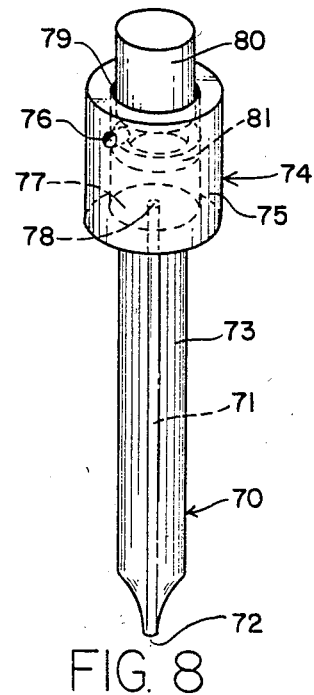
FIG. 8 is a broken side elevational view of another embodiment of a sampling device in accordance with the present invention.
Figure 9:
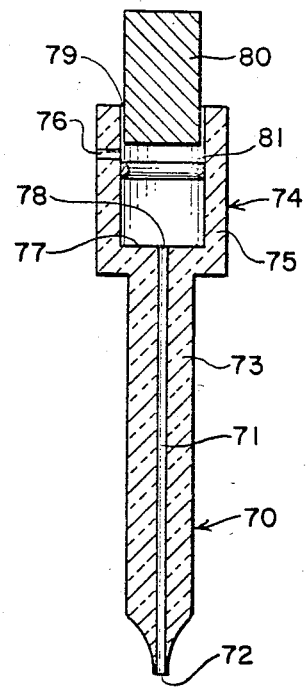
FIG. 9 is a cross-sectional view of the sampling device of FIG. 8.

Another embodiment of the sampling device of the present invention is depicted in FIG. 8 and FIG. 9. Referring now to FIG. 8 and FIG. 9, collection tube 70 has capillary passage 71 with orifice 72 at one end of collection tube 70. Capillary passage 71 is formed in 70 by wall 73. The other end of collection tube 70 is a chamber 74 which may be a separate part (not shown) or an integral part (shown) of collection tube 70. Chamber 74 is defined by wall 75 which has a small opening 76 extending from the exterior of 74 to its interior. Chamber 74 has a base 77 in which capillary passage 71 terminates at 78. Chamber 74 has an opening 79 at its top to accomodate plug 80, which is movably mounted in chamber 74. The dimensions of chamber 74, passage 71 and plug 80 are such as to achieve the collecting and dispensing of a liquid. Plug 80 is in a first position wherein pressure equalization is allowed through opening 76 from the interior of chamber 74 to the exterior of chamber 74 and liquid may enter capillary passage 71. Plug 80 is movable to a second position through sealing means 81 wherein pressure equalization through opening 76 is prevented. As a result any liquid in capillary passage 71 is forced out of the passage through orifice 72.

It is within the scope of the present invention to include a prepackaged breakable capsule within the chamber of the present sampling device. The prepackaged breakable capsule could contain, for example, a predetermined amount of a diluent such as an aqueous buffer which would wash out the liquid in the capillary passage and dilute the liquid quantitatively. The capsule could be fabricated from a suitable breakable material which would be compatible with the ultimate use of the sampling device including the liquid to be sampled. Exemplary of suitable materials for the capsule are glass, breakable plastic, and the like. FIG. 10 depicts the device of FIG. 1 which further contains capsule 90 in chamber 16.

There are also additional advantages which are generally realized by employing the sampling device of the present invention. The present sampling device does not resemble a syringe in that it lacks a needle-like member. Syringes and needles tend to have a disturbing effect on a patient's peace of mind. Secondly, the present sampling device provides a minimum number of manipulative steps to achieve sample collecting and dispensing. The method for collecting and dispensing a sample in accordance with the present invention involves contacting a sample with the collecting and dispensing orifice of the present sampling device. No mechanical action is required. The sample is allowed to traverse the capillary passage by capillary action. The device is then manipulated from a first position to a second position which prevents pressure equilization between the interior and exterior of the chamber. Further manipulation of the device results in removal of the sample from the capillary passage. Basically, then, only two manipulative steps are involved.

Another advantage of the sampling device of the present invention is that no external collection force, such as suction and the like, is required to collect the sample. This advantage is particularly important for a non-syringe-like device for use in collecting very small amounts of a liquid from a small sample. A further advantage of the present device is that it is small and capable of being designed for both precise and imprecise volume collection of a sample. Where a precise or accurate amount of a sample must be dispensed into a system, the present device may be designed to provide such a quantitative amount.

The use of the sampling device of the present invention is illustrated in FIGS. 11-13. Referring to FIG. 11, the sampling device as depicted in FIG. 1 is contacted with a blood drop on the finger of a patient obtained by pricking the patient's finger. In FIG. 11 the blood is shown traversing the capillary passage by capillary action. When capillary action no longer draws blood into the capillary passage, and, thus, a predetermined volume is obtained, the sampling device is removed from the source of the sample and placed in a container as shown in FIG. 12. In this case, the container is filled with a liquid medium with which the dispensed blood will mix. FIG. 13 depicts the blood sample now mixing with the contents of the tube. The blood sample was forced from the sampling device of the invention by movement of housing 15 in the direction of orifice 12. This may be accomplished, e.g., by placing the collecting and dispensing end of the collection tube against the bottom of the container and pushing downward on the top of portion of the device.

The invention has been described in detail with particular reference to the above embodiments. It will be understood, however, that variations and modifications can be effected within the spirit and scope of the invention.

What is claimed is:

1. A sampling device, which comprises—
   a capillary tube having a first orifice for collecting by capillarity a predetermined amount of a liquid and dispensing said predetermined amount of liquid and a second orifice at its other end,
   means defining a chamber enclosing said second orifice,
   an means defining an opening to the outside atmosphere, other than said first orifice, communicating with said capillary tube, and
   substantially rigid means movable with respect to said means defining an opening for concomitantly sealing said opening and forcing air from said chamber through said capillary tube thereby dispensing said predetermined amount of liquid.

2. The device of claim 1 wherein said capillary tube is movable within said chamber.

3. The device of claim 2 which further includes means for frictionally retaining said tube in said chamber.

4. The device of claim 1 wherein said opening is in said means defining a chamber.

5. The device of claim 1 wherein said chamber and said means defining a substantially rigid movable means form a single element.

6. The device of claim 1 wherein said capillary tube is telescopically movable in said chamber.

7. The device of claim 1 which further includes sealing means within said chamber cooperative with said substantially rigid movable means to prevent pressure equalization in said chamber.

8. The device of claim 1 wherein the capacity of said capillary tube is from about 0.1 to 100 microliters.

9. The device of claim 1 which further includes a breakable capsule in said chamber.

10. A sampling device, which comprises—
a collection tube having a capillary passage with an orifice at one end for collecting a predetermined volume of a liquid by capillary action and dispensing said predetermined volume of liquid and a second orifice at the other end thereof,
a means defining a chamber enclosing said second orifice, said means defining a chamber having an opening, in addition to the opening provided by said capillary passage, providing pressure equalization between the interior and exterior of said chamber, and
substantially non-compressible movable means adjacent said second orifice,
said substantially non-compressible movable means means and said tube being in a first position allowing pressure equalization through said opening,
said substantially non-compressible movable means means and said tube being manipulatable to a second position concomitantly preventing pressure equalization through said opening and defining a chamber volume which is greater than said predetermined volume of said capillary passage whereby said predetermined volume of liquid is dispensed from said collection tube.

11. A sampling device, which comprises
a housing,
a collection tube telescopically movable in a chamber in said housing and having a capillary passage and a collection and dispensing orifice at one end and a second orifice at the other end of said tube enclosed by said housing wherein said collection tube has a volume for collecting a liquid therein by capillary action,
said housing having an opening providing for pressure equalization to said chamber thus permitting capillary action along said capillary passage, when said tube and said housing are in an extended position,
said tube and said housing being movable from said extended position to a retracted position concomitantly preventing said pressure equalization through said opening and requiring pressure equalization to said chamber through said capillary passage whereby liquid in said collection tube is dispensed therefrom.

12. The device of claim 11 wherein the dimensions of said chamber and position of said opening are such as to provide a chamber volume, when pressure equalization no longer exists to said chamber through said opening, which volume is greater than a predetermined volume of said capillary passage.

13. A sampling device, which comprises—
a collection tube having a capillary passage with a collecting and dispensing orifice at one end and a second orifice at the other end of said tube wherein said collection tube has a volume for collecting a fluid therein by capillary action
a means defining a chamber enclosing said second orifice, said means defining a chamber having an opening, in addition to said capillary passage, providing pressure equalization of the chamber with respect to the atmosphere, and
substantially non-compressible means for moving at least a portion of said chamber in the direction of said collecting and dispensing orifice and simultaneously sealing said opening and forcing fluid in said means defining a chamber through said passage.

14. The device of claim 13 wherein said chamber and said means for moving form a single element.

15. The device of claim 13 wherein said collection tube is telescopically movable in said chamber.

16. The device of claim 13 wherein the dimensions of said chamber and position of said opening are such as to provide a volume, when said opening is sealed by said substantially non-compressible means means, greater than a predetermined volume of said capillary passage.

17. A device for use in a diagnostic test which comprises—
a housing having front and rear portions,
a diagnostic test device mounted on a portion of said housing,
a collection tube telescopically movable in a chamber in another portion of said housing,
said collection tube having a capillary passage and a collecting and dispensing orifice at one end and a second orifice at the other end of said tube enclosed by said housing,
said housing having an opening providing for pressure equalization to said chamber and permitting capillary flow along said capillary passage,
said tube being movable with respect to said opening to concomitantly seal said opening and force air from said chamber through said capillary passage thereby dispensing said liquid from said collection tube.

18. A sampling device comprising a transparent tube having a narrow bore capillary passage of uniform cross-section extending therethrough, said capillary passage being of a predetermined volumetric capacity within the range of 0.1 to 100 microliters and being fillable under forces of capillary attraction when the intake end thereof is contacted with body of liquid to be sampled, at least the upper end of said tube being movable enclosed within a chamber in a substantially non-compressible housing, said housing having an opening in the wall thereof whereby, when said opening is in communication with the outside of said housing, said capillary passage may be completely filled with a liquid sample of a predetermined volume by inserting the lower end of the device into a body of liquid and whereby, when said opening is sealed by the movement of said housing with respect to said tube and communication with the outside of said housing is prevented, said capillary passage may be completely emptied by further movement of said housing with respect to said tube by forcing air through said capillary passage.

19. A method for collecting and dispensing a sample, using a sample device which comprises:
- a capillary tube having a first orifice for collecting by capillary a predetermined amount of a liquid and dispensing said predetermined amount of liquid and a second orifice at its other end,
- means defining a chamber enclosing said second orifice,
- means defining an opening to the outside atmosphere, other than said first orifice, communicating with said capillary tube, and
- substantially rigid means movable with respect to said means defining an opening for concomitantly sealing said opening and forcing air from said chamber through said capillary tube thereby dispensing said predetermined amount of liquid, said method comprising the steps of:
- contacting the sample with said collecting and dispensing orifice of the device,
- allowing the sample to traverse said capillary tube by capillary action,
- manipulating said substantially rigid movable means with respect to said opening to concomitantly seal said opening and dispense the sample through said collecting and dispensing orifice.

20. A method for collecting and dispensing a sample, using a sampling device which comprises:
- a capillary tube having a first orifice for collecting by capillarity a predetermined amount of a liquid and dispensing said predetermined amount of liquid and a second orifice at its other end,
- means defining a chamber enclosing said second orifice,
- means defining an opening to the outside atmosphere, other than said first orifice, communicating with said capillary tube, and
- substantially rigid means movable with respect to said means defining an opening for concomitantly sealing said opening and forming air from said chamber through said capillary tube thereby dispensing said predetermined amount of liquid, said chamber means and substantially rigid movable means forming a single element, said method comprising the steps of:
- contacting the sample with said collecting and dispensing orifice of the device,
- allowing the sample to traverse said capillary tube by capillary action,
- manipulating said single element with respect to said opening to concomitantly seal said opening and dispense the sample through said collecting and dispensing orifice.

21. A method for collecting and dispensing a sample, using a sampling device which comprises:
- a transparent tube having a narrow bore capillary passage of uniform cross-section extending therethrough, said capillary passage being of a predetermined volumetric capacity within the range of 0.1 to 100 microliters and being fillable under forces of capillary attraction when the intake end thereof is contacted with a body of liquid to be sampled, at least the upper end of said tube being movably enclosed within a chamber in a substantially non-compressible housing, said housing having an opening in the wall thereof whereby, when said opening is in communication with the outside of said housing, said capillary passage may be completely filled with a liquid sample of a predetermined volume by inserting the lower end of the device into a body of liquid, said method comprising the steps of:
- contacting the sample with the intake end of the device,
- allowing the sample to traverse said capillary passage by capillary action, and
- manipulating said housing with respect to said tube whereby said opening is sealed and communication with the outside of said housing is prevented and said capillary passage may be completely emptied by further movement of said housing with respect to said tube by forcing air through said capillary passage.

* * * * *